US012558119B2

(12) United States Patent
Wong

(10) Patent No.: US 12,558,119 B2
(45) Date of Patent: Feb. 24, 2026

(54) PUNCTURE DEVICE

(71) Applicant: Angiomed GmbH & Co.
Medizintechnik KG, Karlsruhe (DE)

(72) Inventor: Kai Chun Wong, Karlsruhe (DE)

(73) Assignee: Angiomed GmbH & Co.
Medizintechnik KG, Karlsruhe (DE)

( * ) Notice: Subject to any disclaimer, the term of this
patent is extended or adjusted under 35
U.S.C. 154(b) by 128 days.

(21) Appl. No.: 18/579,828

(22) PCT Filed: Jul. 16, 2021

(86) PCT No.: PCT/EP2021/069969
§ 371 (c)(1),
(2) Date: Jan. 16, 2024

(87) PCT Pub. No.: WO2023/284978
PCT Pub. Date: Jan. 19, 2023

(65) Prior Publication Data
US 2024/0325046 A1      Oct. 3, 2024

(51) Int. Cl.
*A61B 17/34* (2006.01)
*A61B 90/00* (2016.01)
*A61B 17/00* (2006.01)

(52) U.S. Cl.
CPC .......... *A61B 17/3417* (2013.01); *A61B 90/39*
(2016.02); *A61B 2017/00867* (2013.01); *A61B*
*2017/3454* (2013.01); *A61B 2090/3966*
(2016.02)

(58) Field of Classification Search
CPC ...... A61M 25/0084; A61M 2025/0089; A61M
25/06; A61B 17/3417; A61B 17/34;
(Continued)

(56) References Cited

U.S. PATENT DOCUMENTS 10,307,569 B2    6/2019  Kunis
2006/0184048 A1    8/2006  Saadat
(Continued)

FOREIGN PATENT DOCUMENTS

WO        2015019132 A1    2/2015
WO          21034537 A1    2/2021
WO        2023284978 A1    1/2023

OTHER PUBLICATIONS

Iro, H., et al., "The Erlangen Salivary Gland Project.—Part 1" Endo
Press. ISBN 978-3-89756-149-6. 2007.
(Continued)

*Primary Examiner* — Katherine M Shi
(74) *Attorney, Agent, or Firm* — Rutan & Tucker LLP

(57) ABSTRACT

The present invention relates to a puncture device that is
arranged for being advanced to a puncture site through the
human vasculature, the puncture device comprising: a punc-
ture means, the puncture means comprising a distal end that
is arranged for creating a puncture in a patient's tissue, a
sheath, the sheath being arranged so as to surround the
puncture means, the puncture means being slidably arranged
inside the sheath, a tissue expansion means, the tissue
expansion means being arranged so that it can be selectively
activated, wherein in the activated state, the tissue expansion
means pushes away the patient's tissue to thereby allow a
re-orientation of the puncture means.

11 Claims, 3 Drawing Sheets

(58) Field of Classification Search
CPC ............ A61B 17/3401; A61B 17/3403; A61B
2017/3405; A61B 17/3474; A61B
17/3478; A61B 2017/348; A61B
2017/3482; A61B 2017/3484; A61B
2017/3488; A61B 2017/3486; A61B
2017/3454; A61B 1/00089; A61B
2017/00247; A61B 2017/00867; A61B
2017/320044; A61B 17/3496; A61B
5/150412; A61B 17/02; A61B 17/0281;
A61B 17/0218; A61B 2017/0225; A61B
17/00234
See application file for complete search history.

(56) References Cited

U.S. PATENT DOCUMENTS

| | | |
|---|---|---|
| 2010/0204549 A1 | 8/2010 | Surti |
| 2011/0060182 A1 | 3/2011 | Kassab et al. |
| 2017/0265892 A1 | 9/2017 | Winegar et al. |
| 2017/0266411 A1 | 9/2017 | Rocha-Singh et al. |
| 2017/0319233 A1 | 11/2017 | Fonger et al. |
| 2017/0367728 A1* | 12/2017 | Qu ..................... A61B 17/3417 |
| 2018/0133442 A1 | 5/2018 | Adriaens et al. |
| 2020/0086095 A1 | 3/2020 | Kleinhaus |
| 2021/0068854 A1 | 3/2021 | Wallace et al. |

OTHER PUBLICATIONS

Olympus, "No-Tip Nitinol Baskets" 2018.
Stoeckel, D., et al., "Self-Expanding Nitinol Stents—Material and Design Considerations." NDC, 2003.
PCT/EP2021/069969 filed Jul. 16, 2021 International Preliminary Report on Patentability dated Sep. 28, 2023.
PCT/EP2021/069969 filed Jul. 16, 2021 International Search Report and Written Opinion dated Mar. 21, 2022.

\* cited by examiner

<u>Figure 1</u>
<u>Figure 2</u>
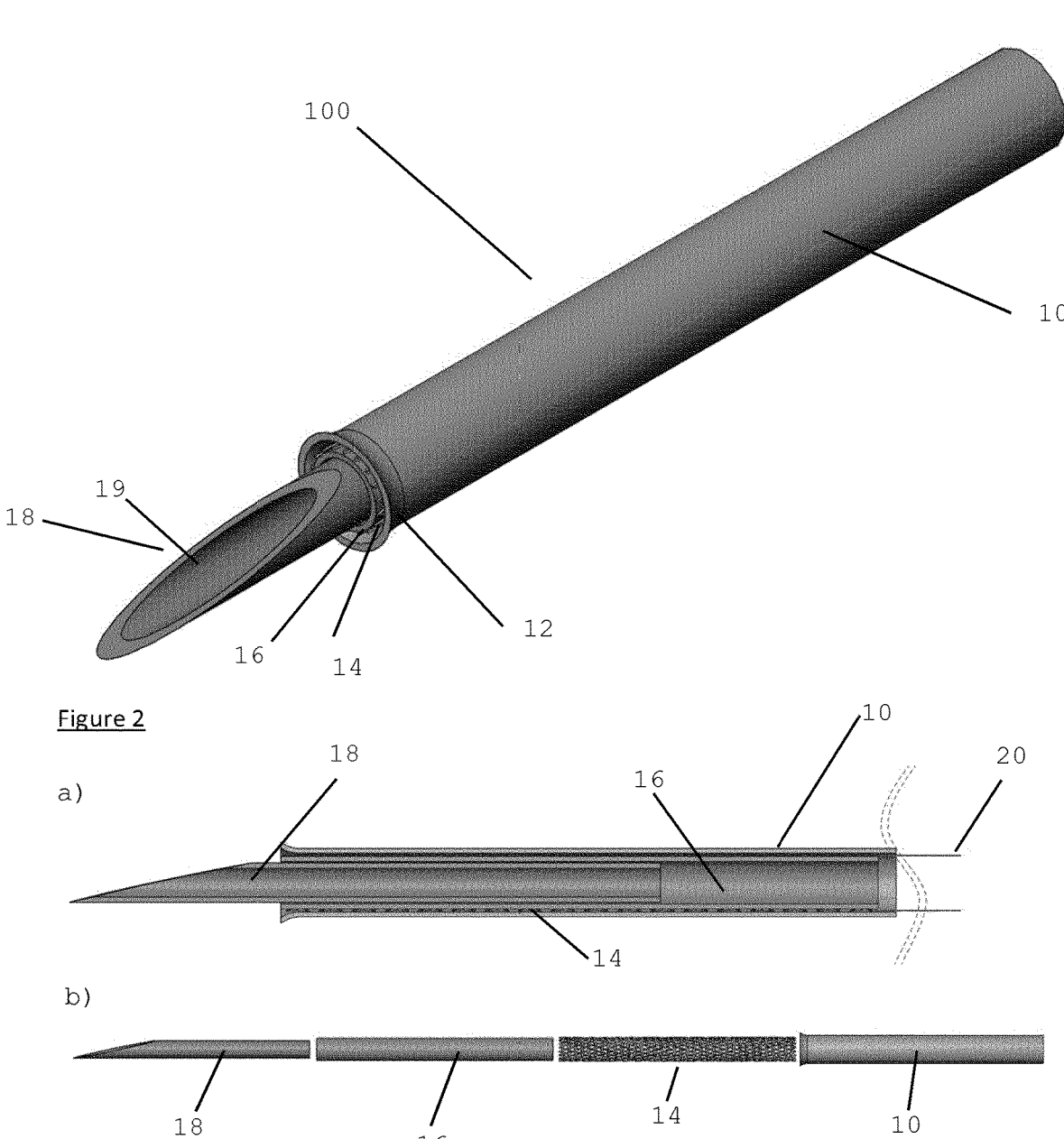

Figure 3

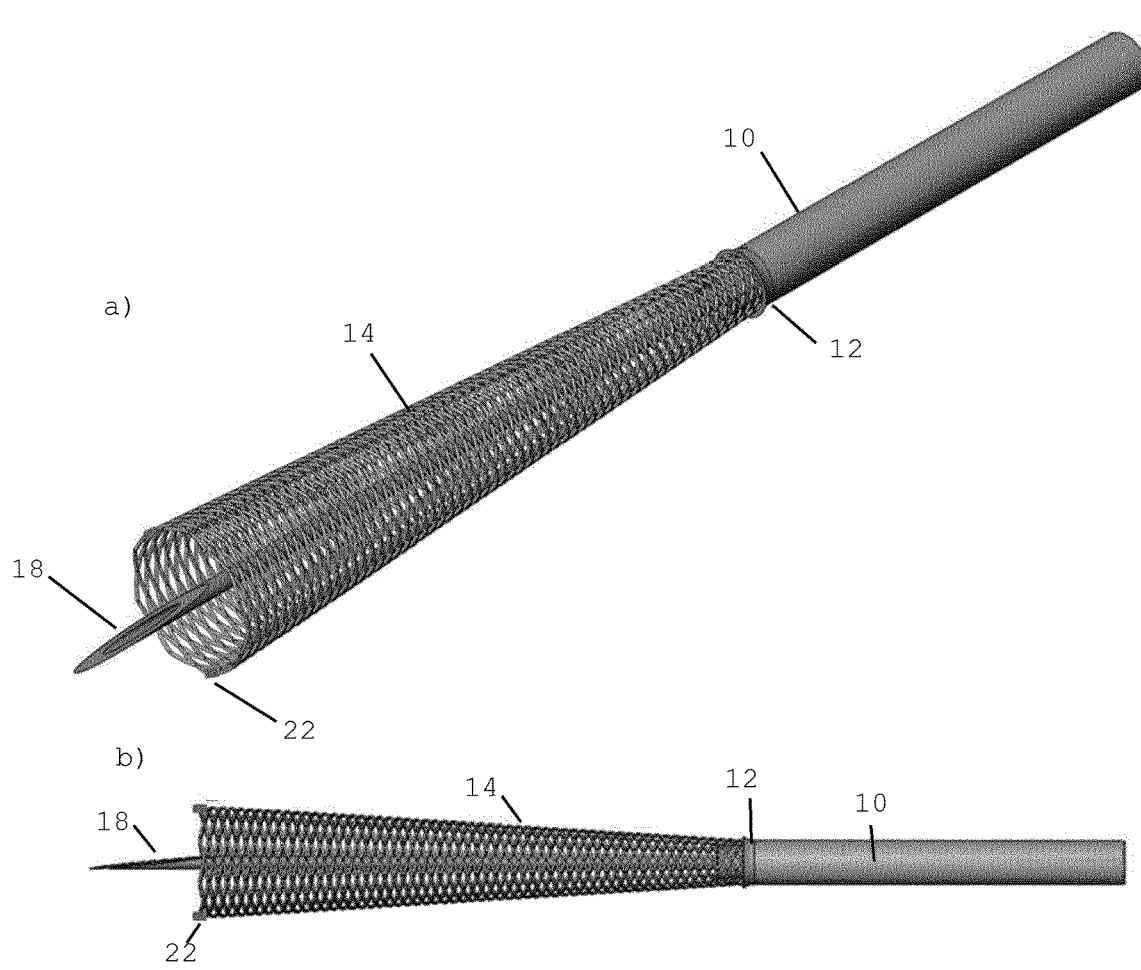

```
┌─────────────────┐
│ Advance puncture│
│ device to punctu│ ──── S110
│ re location     │
└─────────────────┘
         │
         ▼
┌─────────────────┐
│ Attempt a punctu│ ──── S112
│ re              │
└─────────────────┘
         │
         ▼
┌─────────────────┐
│ If unsuccessful:│
│ expand tissue   │ ──── S114
│ expansion means │
└─────────────────┘
         │
         ▼
┌─────────────────┐
│ Reorient punctur│ ──── S116
│ e means         │
└─────────────────┘
         │
         ▼
┌─────────────────┐
│ Attempt puncture│ ──── S118
│ again           │
└─────────────────┘
```

PUNCTURE DEVICE

PRIORITY

This application is a U.S. national stage application of International Application No. PCT/EP2021/069969, filed Jul. 16, 2021, which is incorporated by reference in its entirety into this application.

TECHNICAL FIELD

The present invention relates to a puncture device.

TECHNICAL BACKGROUND

In patients suffering from late stage liver cirrhosis, a treatment that is commonly used is the creation of a TIPS (Transjugular Intrahepatic Portosystemic Shunt) shunt. Such a TIPS shunt is an artificial channel that is created between the hepatic and the portal vein and that allows for blood to bypass the liver. It has been shown that such shunts improve the life expectancy of patients diagnosed with liver cirrhosis since it is a treatment for portal hypertension (which is often due to liver cirrhosis) which frequently leads to intestinal bleeding, life-threatening esophageal bleeding (esophageal varices) and the buildup of fluid within the abdomen (ascites).

Such shunts are typically created by advancing a puncture needle through the patient's vasculature to the puncture site. A surgeon will then puncture the diseased liver tissue with the aim of the puncture reaching the portal vein. If the puncture attempt is unsuccessful, the needle is withdrawn from the patient's vasculature and will be reshaped, for example by manual bending.

Once the TIPS shunt has been created, a specialised TIPS stent graft is placed within the puncture so as to keep it open. Through that shunt, blood can bypass the liver, which ameliorates portal hypertension.

However, it is also to be noted that there are numerous other fields of surgery where puncture devices are needed.

SUMMARY OF THE INVENTION

The present inventor has realised that the creation of a TIPS shunt is often rather complicated. It is frequently the case that the surgeon does not manage to puncture the portal vein on the first attempt. Accordingly, the puncture needle needs to be withdrawn somewhat and rotated (or, in some cases, completely withdrawn and bent). Afterwards, another puncture attempt can be made. It is clear that the time consumption is significant. Furthermore, withdrawing the needle and manually bending it also comes with a risk of injuring the surgeon. Given that a patient's blood can contain pathogens such as viruses, it is thus highly desirable to reduce the number of times a TIPS puncture needle needs to be withdrawn.

It is also often difficult to rotate the puncture needle when inside the patient's vasculature. Diseased liver tissue is generally very congested, so that rotating a bent puncture needle inside the patient is difficult, if not impossible, due to a lack of space. Accordingly, the needle needs to be withdrawn to a less congested space, with a corresponding time consumption. Furthermore, the limited visualization of the space makes the procedure even more complicated.

The present invention aims at alleviating or even solving at least some of those problems.

One embodiment of the invention is defined by claim 1. Additional embodiments are described in the dependent claims. Embodiments described herein relate to a puncture device that is arranged for being advanced to a puncture site through the human vasculature. Accordingly, it needs to be sufficiently low profile and sufficiently flexible for such an advancement. In optional embodiments, the puncture device is sufficiently stiff for penetrating diseased liver tissue.

The puncture device comprises a puncture means which is that component of the puncture device that is meant for creating a puncture through tissue. Such a puncture means can take the form of a hollow needle. The puncture means has a pointed distal end that is arranged for creating a puncture in a patient's tissue.

Furthermore, a sheath is provided. This sheath surrounds the puncture means and has the puncture means slidably arranged inside the sheath. Accordingly, when the puncture device is used for puncturing tissue, and when it is thus inside the human body, the sheath can be slidably moved relative to the puncture means.

The puncture device furthermore comprises a tissue expansion means that is arranged so that it can be selectively activated, wherein when in the activated state, the tissue expansion means pushes away the patient's tissue to thereby allow a reorientation of the puncture means.

Accordingly, with the inventive puncture device, the tissue expansion means can push tissue away so as to create a space within which the puncture means can be reoriented. Thus, the orientation of the puncture means can be changed without having to completely withdraw the puncture means by activating the tissue expansion means and by then rearranging the puncture means, for example by rotating it. Such a puncture device allows for some degree of reorientation of the puncture means and hence minimizes the number of times the puncture device has to be withdrawn during use. This reduces the time required for the puncture procedure.

In embodiments, the tissue expansion means is slidably arranged inside the sheath and is arranged so that it can be slid out of the sheath so as to extend distally relative to the distal end of the puncture means. In that way, the tissue expansion means can be shielded from the outside of the puncture device by means of being inserted into the sheath, which therefore allows for a protection of the expansion means. Furthermore, the sheath can serve as a way of avoiding premature expansion of the expansion means by restraining it. The sheath can in particular be made of polyethylene terephthalate (PET) or polyether ether ketone (PEEK).

According to one embodiment, the tissue expansion means is arranged so as to expand when heated above a threshold temperature to thereby push away tissue. Such a heating up of the tissue expansion means can be achieved, for example by having a heating coil installed as part of the puncture device. Accordingly, this is an easy to implement way of actuating the tissue expansion means of the puncture device.

In some embodiments, the tissue expansion means comprises a shape memory alloy, e.g. nitinol. Such materials are well characterised and find wide application in the technical field of puncture devices and stent/stent grafts. Furthermore, they have good capabilities of creating implants that will expand when heated above a certain threshold temperature.

In that context, in embodiments, there is a means for selectively heating up the tissue expansion means. Such a means, which could take the form of or include a coil, is an easy to implement way of heating up tissue expansion means and can thus be used as a simple actuation mechanism.

In embodiments, the threshold temperature above which the expansion of a tissue expansion means occurs is higher than 37° C., in embodiments higher than 39° C., e.g. of about 40° C. Transition temperatures of 45° C. or even 50° C. can also be used in the case of severely diseased liver. Each° C. change from the transition temperature could change the radial forces by approximately 4 N/mm². By having such a temperature threshold, premature expansion of the tissue expansion means due to heating to body temperature is avoided. Furthermore, choosing a transition temperature that is higher than body temperature ensures that an active heating of the tissue expansion means is needed to keep it in the activated state. Accordingly, if it is no longer desired to use the tissue expansion means, it suffices to no longer actively heat it. In that situation, it will cool down to body temperature and thus no longer be activated. Furthermore, in the context of shape memory alloys, it is known that the higher the transition temperature, the higher the resulting stiffness of the tissue expansion means and hence the higher the force it applies to surrounding tissue (cf. Dieter Stoeckel et al., Eur. Radiol. 2004 February, "Self-Expanding Nitinol Stents-Material and Design Considerations"). Accordingly, having a higher transition temperature leads to a higher force that is applied to the tissue to be pushed away, which increases the space available for reorienting the puncture means. Furthermore, the higher the difference between the transition temperature and body temperature, the easier it is to control the system. In embodiments, a temperature difference of more than 10° C. is envisaged.

In embodiments, the tissue expansion means has, in the activated configuration, a shape where the cross-sectional area of the tissue expansion means increases when moving from a proximal end to a distal end of the tissue expansion means. As used herein, the proximal end is closer to the handle of the puncture device which will be held by the surgeon, whereas the distal end is closest to the tip of the puncture device. By having such a shape where the cross-sectional diameter increases, the area over which a rearrangement of the puncture device can be achieved increases, which gives greater manoeuvrability for the puncture device.

In embodiments, the tissue expansion means can be brought back to its non-activated state (which a correspondingly reduced cross-sectional diameter) by means of advancing the sheath relative to the puncture device and thus relative to the tissue expansion means. This makes it easier to reduce the cross-sectional diameter of the tissue expansion means when needed.

In embodiments, the tissue expansion means comprises an expandable lattice structure similar to that of a stent. Since such stents have been well-characterised and are used widely in medicine, the generally well-known manufacturing techniques for such devices can also be supplied to such tissue expansion means.

According to an alternative embodiment, a puncture device comprises:

a needle including a sharp distal end configured for puncturing tissue;

a sheath surrounding the needle, the sheath slidable relative to the needle; and an expansion component slidable relative to the needle and the sheath, the expansion component configured to be selectively activated from a dormant state to an activated state, the expansion component providing space for re-orientation of the needle in the activated state.

BRIEF DESCRIPTION OF THE DRAWINGS

FIG. 1: shows a puncture device according to a first embodiment of the invention.

FIG. 2a shows a longitudinal sectional view of the puncture device of FIG. 1.

FIG. 2b shows components of the puncture device of FIG. 2a.

FIG. 3 shows the puncture device according to the first embodiment in a deployed configuration.

FIG. 5 shows steps in the use of the puncture device of the first embodiment.

DETAILED DESCRIPTION OF THE DRAWINGS

Figure 4:
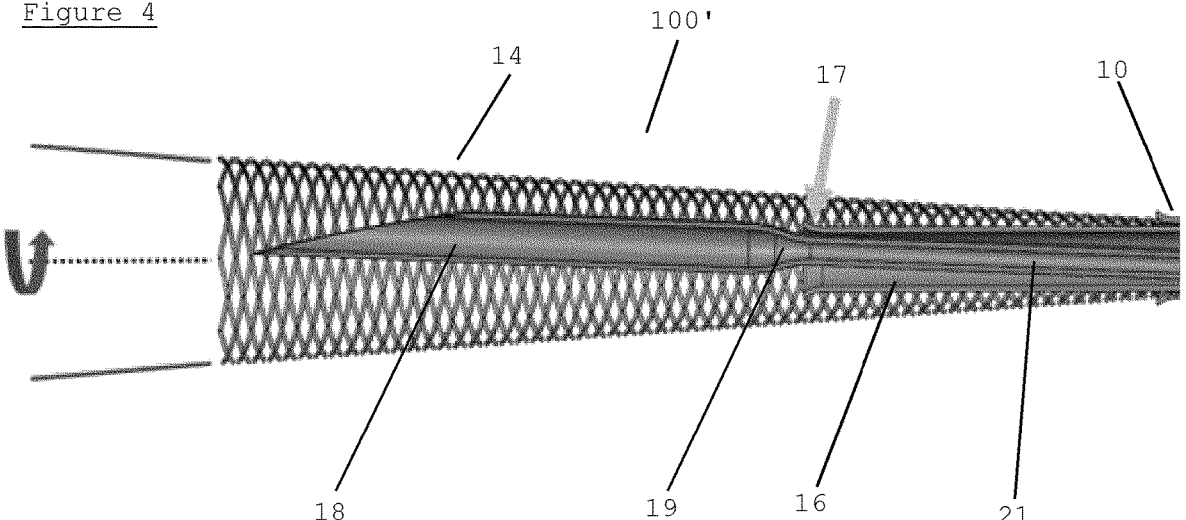
FIG. 4 shows the puncture device according to a second embodiment.

FIG. 1 shows a puncture device according to a first embodiment of the present invention. The puncture device 100 comprises a puncture means 18 that has the form of a hollow needle a having lumen 19 extending longitudinally therethrough. This lumen 19 can be used for aspirating blood to check whether a puncture attempt has been successful.

Provided so as to surround the puncture means 18 is a tube 16. This tube 16 serves to prevent the puncture means 18 from coming into contact with those components of the puncture device 100 that are further towards the outside.

The tube 16 is surrounded by a tissue expansion means 14 that has the shape of a tubular mesh work made of nitinol. The whole assembly of the puncture means 18, tube 16 and tissue expansion means 14 is surrounded by a sheath 10. The sheath 10 has, at its distal end, a flared-out distalmost end 12 that corresponds to a widening opening. The sheath 10 is slidable relative to the puncture means 18 as well as relative to the tube 16 and the tissue expansion means 14.

FIG. 2a) shows a longitudinal cross-section of what is shown in FIG. 1. As can be seen, the puncture means 18 extends distally from the distal most ends of the sheath 10, the tube 16, and the tissue expansion means 14. As can be furthermore seen, wires 20 are connected to a proximal end of the puncture device. Using electricity conducted through those wires 20, a heating means (not shown) can be heated up which will cause the tissue expansion means 14 to heat up and to thus expand to thereby push away patient tissue surrounding it.

In FIG. 2b), some of the components described previously with respect to FIG. 2a) have been shown. As can be seen, a sheath 10, a tissue expansion means 14, a tube 16 and a puncture means 18 are arranged inside the puncture device 100 which can, as shown in FIG. 2a), be arranged concentrically.

FIG. 3 shows a configuration in which the tissue expansion means 14 has been positioned distally relative to the sheath 10. In that configuration, in which the tissue expansion means 14 has also expanded outwardly, the tissue expansion means 14 assumes a flared-out shape that is similar to a trumpet. The widest diameter portion is at that position of the tissue expansion means 14 that is furthest away from the sheath 10. Any tissue that would surround the tissue expansion means 14 will be pushed away in the circumferential and/or radial direction, resulting in free space for reorienting the puncture means 18. Accordingly, in that configuration, if a puncture attempt of the portal vein has been unsuccessful, the puncture means 18 can be reoriented, and another puncture attempt can be made.

What can also be seen from FIG. 3 are radiopaque markers 22 that are provided at the distalmost end of the tissue expansion means 14. They serve to localise the tissue expansion means 14 inside a body and aid a surgeon in knowing where in the body the puncture device is arranged. They can be visualized using, for example, radiography. Such markers can use tantalum or gold as the radiopaque material. The radiopaque markers 22 aid in indirectly localizing the puncture means 18 since they surround the puncture means 18.

The tissue expansion means 14 can be brought into this expanded state by means of proximally withdrawing the sheath 10 whilst activating the non-illustrated heating means by means of conducting electricity through the wires 20. When the tissue expansion means 14 is heated above the transition temperature of nitinol, it will expand to its expanded state, which is illustrated in FIGS. 3a), b). Any bodily tissue that surrounds the tissue expansion means 14 will thus be pushed away in the radial and/or circumferential direction. Accordingly, the puncture means 18 can be reoriented comparatively freely. It is to be noted that a portion of the tissue expansion means 14 stays underneath the sheath 10 even when the tissue expansion means 14 is expanded so as to aid in compressing and, finally, retracting it.

If the tissue expansion means 14 is to be reduced in its diameter, for example if it is to be withdrawn, it will be sufficient to advance the sheath 10 relative to the tissue expansion means 14 whilst also ensuring that heating means provided as part of the puncture device 100 is deactivated. The tissue expansion means 14 will quickly cool down so that it be comparatively easy retracted into the sheath 10. The flared-out distalmost end 12 will act so as to aid in compressing the expansion means 14 so that it can be retracted and retained inside the sheath 10. If need be, the tissue expansion means 14 can be redeployed as described in the previous paragraph.

FIG. 4 shows a puncture device 100' according to a second embodiment of the invention. It is to be noted that the same reference numerals will be used that were also used when describing the first embodiment, and a detailed description of the corresponding components will be omitted.

As can be seen from FIG. 4, the puncture means 18 does not have a uniform cross-section but becomes thinner at a thinning portion 19 when moving from the distal end of the puncture means 18 to the proximal end. Furthermore, the tube 16 has a flared-out portion 17 at its distal end. By the puncture means 18 becoming thinner at the thinning portion 19, the distal end of the puncture means 18 can have a greater degree of bent, which gives a greater degree of freedom for a surgeon when reorienting it by rotating the puncture means 18 as indicated by the arrow. The flared-out portion 17 makes it easier to retract the puncture means 18 into the tube 16. The maximum degree of freedom is defined by the angle between the expanded tissue expansion means 14 and the center line (which is indicated by a dashed line).

FIG. 5 shows steps in the use of the puncture device according to the present invention.

As a first step (step S110), the puncture device is advanced, typically through a patient's vasculature, to an intended puncture location.

Subsequently (step S112), the surgeon attempts a puncture. If desired, it can be checked whether the puncture was successful by means of aspirating blood through a lumen of the puncture means of the puncture device. If successful, further procedures such as the placement of a device such as the TIPS stent graft take place.

If, however, the puncture attempt is unsuccessful, in step S114, the tissue expansion means is expanded so as to push away tissue to thereby create a space for reorienting the puncture means.

Subsequently (step S116), the puncture means is reoriented and brought into a position that is, in the surgeon's assessment, more likely to result in a successful puncture.

Subsequently (step S118), another puncture attempt is made. If this step is unsuccessful, steps S116 and S118 can be performed repeatedly, until the surgeon succeeds in puncturing the blood vessel to be punctured. Subsequently (not shown in the flow chart), once the shunt has been created, the tissue expansion means 14 is retrieved, as is the rest of the puncture device, whilst typically leaving a guidewire in place to aid in placing an implant.

It is to be noted that whilst in the previous description, an emphasis was placed on tissue expansion means 14 that use shape memory alloys, it would also be an option to use other means. In particular, balloons that can be expanded by means of being inflated are also being considered as tissue expansion means.

The invention claimed is:

1. A puncture device that is arranged for being advanced to a puncture site through a human vasculature, the puncture device comprising:
   a puncture means, the puncture means comprising a distal end that is arranged for creating a puncture in a patient's tissue,
   a sheath, the sheath being arranged so as to surround the puncture means, the puncture means being slidably arranged inside the sheath, and
   a tissue expansion means, the tissue expansion means being arranged so that it can be selectively activated, wherein in an activated state, the tissue expansion means is configured to push away the patient's tissue to thereby allow a re-orientation of the puncture means, the tissue expansion means being arranged so as to expand when heated above a threshold temperature to thereby push away the patient's tissue, the tissue expansion means comprising a shape memory alloy.

2. The puncture device according to claim 1, the tissue expansion means being slidably arranged inside the sheath and being arranged so that it can be slid out of the sheath so as to extend distally relative to the distal end of the puncture means.

3. The puncture device according to claim 1, further comprising a means for selectively heating up the tissue expansion means.

4. The puncture device according to claim 1, the threshold temperature being higher than 37° C.

5. The puncture device according to claim 1, the tissue expansion means being arranged so that in the activated state, it assumes a shape having a cross-sectional area that increases when moving from a proximal end to a distal end of the tissue expansion means.

6. The puncture device according to claim 1, wherein the tissue expansion means is arranged so that it can be reduced to its non-activated state by means of advancing the sheath relative to the tissue expansion means.

7. The puncture device according to claim 1, wherein the tissue expansion means comprises an expandable lattice structure.

8. The puncture device according to claim 1, wherein the puncture means has a non-uniform cross-sectional diameter, with the non-uniform cross-sectional diameter decreasing when moving from the distal end to a proximal end of the puncture means.

9. The puncture device according to claim 1, the sheath having a flared-out distal-most portion.

10. The puncture device according to claim 1, further comprising a tube arranged between the puncture means and the tissue expansion means.

11. The puncture device according to claim 10, the tube comprising a flared-out portion at its distalmost end.

* * * * *